United States Patent [19]

Gaffar et al.

[11] Patent Number: 4,627,977

[45] Date of Patent: Dec. 9, 1986

[54] ANTICALCULUS ORAL COMPOSITION

[75] Inventors: Abdul Gaffar, Princeton; Thomas G. Polefka, Somerset, both of N.J.

[73] Assignee: Colgate-Palmolive Company, New York, N.Y.

[21] Appl. No.: 775,851

[22] Filed: Sep. 13, 1985

[51] Int. Cl.$^4$ .................. A61K 7/16; A61K 7/18; A61K 9/68

[52] U.S. Cl. ...................... 424/52; 424/48; 424/57

[58] Field of Search .................... 424/49–58

[56] References Cited

U.S. PATENT DOCUMENTS

| | | | |
|---|---|---|---|
| 3,429,963 | 2/1969 | Shedlovsky | 424/56 |
| 3,699,220 | 10/1972 | Westrate et al. | 424/52 |
| 3,927,201 | 12/1975 | Baines et al. | 424/54 |
| 3,927,202 | 12/1975 | Harvey et al. | 424/57 |
| 3,932,603 | 1/1976 | Haas | 424/49 |
| 3,956,480 | 5/1976 | Dichter et al. | 424/49 |
| 3,957,967 | 5/1976 | L'Orange | 424/48 |
| 4,046,872 | 9/1977 | Mitchell et al. | 424/52 |
| 4,075,317 | 2/1978 | Mitchell et al. | 424/52 |
| 4,138,477 | 2/1979 | Gaffar | 424/52 |
| 4,183,914 | 1/1980 | Gaffar et al. | 424/49 |
| 4,217,343 | 8/1980 | Gaffar et al. | 424/49 |
| 4,255,414 | 3/1981 | Lembke et al. | 424/50 |
| 4,357,318 | 11/1982 | Shah et al. | 424/52 |
| 4,460,565 | 7/1984 | Westrate et al. | 424/57 |
| 4,515,772 | 5/1985 | Parran | 424/57 |
| 4,537,765 | 8/1985 | Gaffar et al. | 424/53 |
| 4,590,066 | 5/1986 | Parran et al. | 424/52 |

*Primary Examiner*—Shep K. Rose
*Attorney, Agent, or Firm*—Herbert S. Sylvester; Murray M. Grill; Robert L. Stone

[57] ABSTRACT

An oral composition such as a toothpaste (including gel or cream), mouthwash, lozenge, chewing gum or tooth powder containing a calculus-inhibiting amount of a linear molecularly dehydrated polyphosphate salt and, to inhibit enzymatic hydrolysis of said polyphosphate salt in saliva, a combination of a fluoride ion-providing source and a synthetic linear polymeric polycarboxylate.

11 Claims, No Drawings

ANTICALCULUS ORAL COMPOSITION

This invention relates to oral compositions containing an anticalculus agent.

Calculus is a hard, mineralized formation which forms on the teeth. Regular brushing aids in preventing a rapid buildup of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline HAP is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including HAP. It is apparent therefore that agents which effectively interfere with crystalline growth of HAP will be effective as anticalculus agents. A suggested mechanism by which the anticalculus agents of this invention inhibit calculus formation probably involves an increase of the activation energy barrier thus inhibiting the transformation of precursor amorphous calcium phosphate to HAP.

Studies have shown that there is a good correlation between the ability of a compound to prevent HAP crystalline growth in vitro and its ability to prevent calcification in vivo, provided of course that such compound is stable in and inert to saliva and its components.

It is well known in the art that water soluble hexametaphosphates, tripolyphosphates and pyrophosphates and the like are effective calcium and magnesium ion suppressors, inhibitors, sequestrants and/or chelating agents, and are effective inhibitors of HAP formation in vitro. U.S. Pat. No. 4,515,772 issued May 7, 1985 to Parran et al discloses and claims oral anticalculus compositions containing a fluoride ion source and soluble dialkali metal pyrophosphates alone or admixed with tetraalkali metal pyrophosphates. The voluminous number of acknowledged prior art and "References Cited" in this patent indicate the many uses and functions of these polyphosphates hitherto proposed in oral compositions.

However, as in part admitted in the aforesaid patent disclosure and as shown hereinafter, these linear molecularly dehydrated polyphosphates (i.e. hexametaphosphates, tripolyphosphates, pyrophosphates, etc.) in common, when introduced into the oral cavity and/or saliva are significantly hydrolyzed by salivary enzymes (phosphatases) to orthophosphates which are ineffective as inhibitors of HAP formation.

It is an object of this invention to provide an improved anticalculus oral composition which will not be subject to one or more of the above problems and disadvantages.

A further object of the invention is to provide an oral composition which inhibits the transformation of amorphous calcium phosphate to HAP crystal structure normally associated with calculus.

Another object of this invention is the provision of an improved method for inhibiting the formation of calculus.

Other objects and advantages will appear as the description proceeds.

In accordance with certain of its aspects, this invention relates to an oral composition containing in an orally acceptable vehicle an effective anticalculus amount of one or a mixture of linear molecularly dehydrated polyphosphate salts as essential anticalculus agent, and as combination inhibitor against enzymatic hydrolysis of said agent in saliva, an amount of a fluoride ion source sufficient to supply about 25–2,000 ppm of fluoride ions and about 0.05–3% of a synthetic anionic linear polymeric polycarboxylate having a molecular weight of about 1,000 to about 1,000,000.

Compounds providing a source of fluoride ion have been profusely disclosed in the prior art as anti-caries agents but not for inhibiting salivary hydrolysis of the linear polyphosphate salts employed herein as anticalculus agents. Synthetic anionic linear polymeric polycarboxylates and their complexes with various cationic germicides, zinc and magnesium have been previously disclosed as anticalculus agents per se in, for example U.S. Pat. No. 3,429,963 to Shedlovsky and instant assignee, U.S. Pat. No. 4,152,420 to Gaffar and instant assignee, U.S. Pat. No. 3,956,480 to Dichter et al and instant assignee, U.S. Pat. No. 4,138,477 to Gaffar and instant assignee, and U.S. Pat. No. 4,183,914 to Gaffar et al. None of these patents however nor any other known prior art, discloses use of such polycarboxylates alone for inhibiting salivary hydrolysis of said linear polyphosphates, much less in combination with a compound providing a source of fluoride ion. It is to be understood that the synthetic anionic linear polymeric polycarboxylates per se disclosed in these patents are operative in the compositions and methods of this invention and such disclosures are to that extent incorporated herein by reference thereto.

The linear molecularly dehydrated polyphosphate salts operative herein as anticalculus agents are well known, being generally employed in the form of their wholly or partially neutralized water soluble alkali metal (e.g. potassium and preferably sodium) or ammonium salts, and any mixtures thereof. Representative examples include sodium hexametaphosphate, sodium tripolyphosphate, disodium diacid, trisodium monoacid and tetrasodium pyrophosphates and the like. Linear polyphosphates correspond to $(NaPO_3)_n$ where n is about 2 to about 125. They are generally employed in the instant oral compositions in approximate weight amounts of 0.1 to 7%, preferably 0.1 to 6%, more preferably 2 to 6%. When n is at least 3 in $(NaPO_3)_n$, said polyphosphates are glassy in character.

The synthetic anionic linear polymeric polycarboxylates operative herein are likewise, as indicated above, well known, being employed in the form of their partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), A.N. 119 (M.W. 250,000) and preferably S-97 Pharmaceutical Grade (M.W. 70,000), of GAF Corporation. The terms "synthetic" and "linear" are intended to exclude known thickening or gelling agents comprising carboxymethylcellulose and other derivatives of cellulose and natural gums, as well as the Carbopols, of reduced solubility due to cross-linkages. Also excluded are the zinc, magnesium and similar metal complexes of these polymeric polycarboxylates.

Other operative polymeric polycarboxylates include those disclosed in U.S. Pat. No. 3,956,180 referred to above, such as the 1:1 copolymers of maleic anhydride with ethyl acrylate, hydroxyethyl methacrylate, N-vinyl-2-pyrrollidone, or ethylene, the latter being available for example as Monsanto EMA No. 1103, M.W. 10,000, and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. Nos. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

The synthetic anionic linear polymeric polycarboxylate component is mainly a hydrocarbon with optional halogen and O-containing substituents and linkages as present in for example ester, ether and OH groups, and is generally employed in the instant compositions in approximate weight amounts of 0.05 to 3%, preferably 0.05 to 2%, more preferably 0.1 to 2%. Amounts in the upper portions of these ranges are typically employed in dentifrice compositions, meaning oral compositions generally containing a dental abrasive and used in conjunction with brushing of the teeth, e.g. tooth pastes, gels, creams and powders. Amounts in excess of these ranges may be employed for thickening or gelling purposes.

The source of fluoride ions, or fluorine-providing compounds, required according to this invention as an essential component of the described inhibitor combination, are well known in the art as anti-caries agents and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium fluorsilicate, ammonium fluorosilicate, sodium fluorozirconate, sodium monofluoro-phosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a nontoxic amount, generally about 0.005 to about 3.0% in the preparation. In a dentifrice preparation, e.g. gel, cream, toothpaste or toothpowder, an amount of such compound which releases up to about 2,000 ppm of F ion by weight of the preparation is considered satisfactory. Any suitable minimum amount of such compound may be used, but it is preferable to employ sufficient compound to release about 300 to about 2,000 ppm, more preferably about 800 to about 1,500 ppm of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1-3%, more typically about 0.76%.

In oral preparations such as mouthwashes, lozenges and chewing gum, the fluorine-providing compound is typically present in an amount sufficient to release up to about 500 ppm, preferably about 25 to about 300 ppm by weight of fluoride ion. Generally about 0.005 to about 1.0 wt.% of such compound is present.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain other desirable forms of this invention, the oral composition may be substantially solid or pasty in character, such as toothpowder, a dental tablet, a toothpaste, gel or dental cream. The vehicle of such solid or pasty oral preparations generally contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 3,070,510 of Dec. 15, 1962 such as melamine-, phenolic-, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 cm.$^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100 and alkali metal alumino-silicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than about 1% of the material is larger than about 37 microns.

The polishing material is generally present in the solid or pasty compositions in weight concentrations of about 10% to about 99%. Preferably, it is present in amounts ranging from about 10% to about 75% in toothpaste, and from about 70% to about 99% in toothpowder.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol (e.g. 400–600) exemplify suitable humectants/carriers. Also advantageous are liquid mixtures of water, glycerine and sorbitol. In clear gels where the refractive index is an important consideration, about 3–30 wt.% of water, 0 to about 80 wt.% of glycerine, and about 20–80 wt.% of sorbitol is preferably employed.

Toothpastes, creams and gels typically contain a natural or synthetic thickener or gelling agent in proportions of about 0.1 to about 10, preferably about 0.5 to about 5, wt.%. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, gum tragacanth, starch, polyvinylpyrrolidone, hydroxyethypropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the oral preparations of this invention such as whitening agents, preservatives, silicones, chlorophyll compounds, other anticalculus agents, and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with the active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, APM (aspartyl phenyl alanine, methyl ester), saccharine and the like. Suitably, flavor and sweetening agents may together comprise from about 0.1% to 5% more of the preparation.

In the preferred practice of this invention an oral composition according to this invention such as a mouthwash or dentifrice containing the described polyphosphate and inhibitor combination in an amount effective to inhibit calculus on dental surfaces is preferably applied regularly to dental enamel, such as every second or third day or preferably from 1 to 3 times daily, at a pH of about 4.5 to about 9, generally about 5.5 to about 8, preferably about 6 to 8, for at least 2 weeks up to 8 weeks or more up to lifetime.

The compositions of this invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The following examples are further illustrative of the nature of the present invention, but it is understood that the invention is not limited thereto. All amounts and proportions referred to herein and in the appended claims are by weight and temperatures are in degrees C. unless otherwise indicated.

EXAMPLE A

Effect of Salivary Enzymes on Inhibition of HAP Formation by HMP* and TSPP**

The in vitro formation of HAP is measured titrimetrically via a pH stat procedure. Stock solutions of 0.1M $CaCl_2$ and 0.1M $NaH_2PO_4$ are prepared fresh in carbonate-free deionized distilled water. To 23 ml $CO_2$-free deionized distilled water 1.0 ml. of the stock phosphate solution and 1.0 ml. of an aqueous solution of $1 \times 10^{-4}M$ of the anticalculus agent being tested are added followed by 1.0 ml. of the stock calcium chloride solution which initiates the reaction. The reaction is conducted at pH 7.4 under a nitrogen atmosphere. Consumption of 0.1N NaOH is recorded automatically from which the time required for crystal formation is determined. Table A shows the results of this procedure.

TABLE A

| Anticalculus Agent | Time of Crystal Growth Inhibition (Hrs.) | | | |
|---|---|---|---|---|
| | Water | Saliva | Pyrophosphatase | Alk. Phosphatase |
| HMP* | >12 | >3 | 1.0 | 2.0 |

TABLE A-continued

| Anticalculus Agent | Time of Crystal Growth Inhibition (Hrs.) | | | |
|---|---|---|---|---|
| | Water | Saliva | Pyrophosphatase | Alk. Phosphatase |
| TSPP** | 0.8 | 0.4 | 0.3 | 0.0 |

*Sodium hexametaphosphate
**Tetrasodium pyrophosphate

Table A shows that in water both agents significantly delay HAP formation. However, the effectiveness of these agents is drastically reduced when incubated with saliva as evidenced by the shorter delay time. This reduction in efficacy is due to the enzymatic hydrolysis of P-O-P bonds. Incubation of these agents with pyrophosphatase and alkaline phosphatase drastically reduces the delay period and indicates the susceptibility of the P-O-P bond to hydrolysis by phosphatases.

EXAMPLE 1

Stabilization of TSPP, STPP* and HMP to Enzymatic Hydrolysis in Presence of Inhibitors Enzymatic hydrolysis is conducted in 100 millimolar morpholinopropane sulfonic acid-NaOH buffer solution (pH 7.0) containing 1.3 mg./ml. of the respective polyphosphate. Inhibitors of this invention are added (except to the control) to a final concentration of 1,000 ppm fluoride ion (from NaF) and 0.5% of the sodium salt of hydrolyzed methoxyethylene-maleic anhydride (1:1) copolymer, M.W. 70,000 (Gantrez S-97 Pharmaceutical Grade). Equal activities of acid, alkaline and inorganic pyrophosphatase are then added to yield a total phosphatase activity of 0.3 units/ml. Samples of each test solution are taken and total orthophosphate available in each sample measured after 3 hours hydrolysis in 4N HCl at 100° C. The reaction mixtures are incubated at 37° C. with shaking and aliquots taken at appropriate times through at least 90 minutes for orthophosphate determination. Table 1 shows the results expressed as percent orthophosphate released due to hydrolysis of the polyphosphate.

TABLE 1

| Anticalculus Agent | Percent Orthophosphate Released in 90 min. | | Percent Relative Protection |
|---|---|---|---|
| | Control | With Inhibitors | |
| TSPP* | 98 | 58 | 41 |
| STPP* | 100 | 62 | 39 |
| HMP | 95 | 40 | 57 |

*Sodium tripolyphosphate

Table I shows that after 90 min. incubation in the presence of enzyme greater than 95% of the available orthophosphate is released from the polyphosphates in the absence of the inhibitors. With inhibitors, hydrolysis of P-O-P bonds in pyrophosphate, tripolyphosphate, and hexametaphosphate is reduced by 41%, 39% and 57%, respectively. It should be noted that the enzyme activities used in this study are at least 2-3 fold greater than those normally found in saliva. These data indicate that the combination of inhibitors of this invention significantly reduces enzymatic hydrolysis of the linear polyphosphates.

EXAMPLE 2

Dentifrice Composition

TABLE 2

| A. Ingredient | Parts |
| --- | --- |
| Deionized water | 37.578 |
| Glycerine | 25.000 |
| Zeo 49B (Silicon Dioxide) | 21.500 |
| HMP (Hexaphos) | 6.000 |
| Syloid 244 (synthetic silica) | 3.000 |
| Sodium Lauryl Sulfate | 1.200 |
| Flavor | 1.000 |
| Gantrez (S-97 Pharmaceutical Grade) | 1.000 |
| Sodium Hydroxide (50% Solution) | 1.000 |
| Xanthan Gum | 1.000 |
| Sodium Benzoate | 0.500 |
| Titanium Dioxide | 0.500 |
| Sodium Saccharin | 0.300 |
| Sodium Fluoride | 0.242 |

B. Formulation of A above but containing TSPP instead of HMP.

C. Formulation of A above but containing 5 parts of STPP instead of 6 parts of HMP.

EXAMPLE 3

Mouthwash

| | Parts |
| --- | --- |
| TSPP | 3.0 |
| Ethyl Alcohol | 15.0 |
| Gantrez S-97 | 0.05 |
| Glycerol | 10.0 |
| Flavor | 0.4 |
| Sodium saccharin | 0.03 |
| NaF | 0.05 |
| Pluronic F 108* | 2.0 |
| Deionized Water to Q.S. | 100 |

*Polyoxyethylenated polyoxypropylene nonionic block polymer surfactant.

EXAMPLE 4

Lozenges

| | Parts |
| --- | --- |
| Sugar | 75-98 |
| Cornsyrup | 1-20 |
| Flavor oil | 0.1-1.0 |
| Tablet lubricant | 0.1-5 |
| Polyphosphate | 0.1-5 |
| Gantrez polymer | 0.05-3 |
| NaF | 0.01-0.05 |
| Water | 0.01-0.2 |

EXAMPLE 5

Chewing Gum

| | Parts |
| --- | --- |
| Gum base | 10 to 50 |
| Binder | 3 to 10 |
| Filler (sorbitol, mannitol or combination thereof) | 5 to 80 |
| Artificial sweetener | 0.1 to 5 |
| Polyphosphate | 0.1 to 5 |
| Gantrez polymer | 0.1 to 1.0 |
| NaF | 0.01-0.05 |
| Flavor | 0.1 to 5 |

This invention has been described with respect to certain preferred embodiments and it will be understood that modifications and variations thereof obvious to those skilled in the art are to be included within the purview of this application and the scope of the appended claims.

We claim:

1. A method of inhibiting dental calculus comprising applying to teeth a calculus-inhibiting amount of a dentifrice composition having a pH of about 4.5 to about 9 containing, in an orally acceptable vehicle, approximately by weight, 0.1 to 7% of one or a mixture of linear molecularly dehydrated polyphosphate salts selected from the group consisting of water soluble alkali metal pyrophosphates, tripolyphosphates and hexametaphosphates, a dentally acceptable silica polishing material, and for the purpose of inhibiting hydrolysis of P-O-P bonds in said polyphosphate salts by phosphatase enzymes in saliva to orthophosphates which are relatively ineffective as inhibitors of hydroxyapatite formation, an amount of a fluorine ion source sufficient to supply 25 ppm. to 2,000 ppm. of fluoride ions and 0.05% to 3% of a water-soluble alkali metal or ammonium synthetic anionic linear polymeric polycarboxylate salt having a molecular weight of about 1,000 to about 1,000,000 said composition when so applied to teeth being effective to inhibit dental calculus.

2. A method effective for inhibiting dental calculus comprising applying to teeth a calculus-inhibiting amount of a toothpaste, gel or cream formulation made with, approximately by weight:
    (a) 2-6% of water soluble tetraalkali metal pyrophosphate,
    (b) an amount of a fluoride ion source sufficient to supply 300 ppm. to 2,000 ppm of fluoride ions,
    (c) 0.1 to 2% of a water soluble alkali metal or ammonium salt of a copolymer of vinyl methyl ether and maleic acid or anhydride having a molecular weight of about 30,000 to about 500,000, and
    (d) an orally acceptable vehicle containing water, humectant and about 10 to 75% of silica dental polishing material, said formulation when so applied to teeth being effective for inhibiting dental calculus.

3. A method effective for inhibiting dental calculus comprising brushing teeth with a calculus-inhibiting amount of a toothpaste, gel or cream formulation made with, approximately by weight:
    (a) 6% of water soluble tetraalkali metal pyrophosphate,
    (b) an amount of a fluoride ion source sufficient to supply 800 ppm to 1,500 ppm. of fluoride ions,
    (c) 1% of a sodium salt of a hydrolyzed copolymer of vinyl methyl ether and maleic acid or anhydride having a molecular weight of about 70,000, and
    (d) an orally acceptable vehicle containing water, humectant and about 10 to 75% of silica dental polishing material, said formulation when so used for brushing teeth being effective for inhibiting dental calcus.

4. A method according to claim 1 wherein said fluoride ion source comprises sodium fluoride.

5. A method according to claim 4 wherein said linear polymeric polycarboxylate comprises a copolymer of vinyl methyl ether and maleic acid or anhydride.

6. A method according to claim 5 wherein said copolymer has a molecular weight of about 30,000 to about 500,000.

7. A method according to claim 5 wherein said polyphosphate salt comprises a sodium pyrophosphate.

8. A method according to claim 1 wherein said composition comprises at least one member of the group consisting of dialkalimetal diacid pyrophosphate, trialkali metal monoacid pyrophosphate and tetraalkali metal pyrophosphate.

9. A method according to claim 8 wherein said alkali metal in said pyrophosphates is independently sodium or potassium.

10. A method as defined in claim 6 wherein said composition contains about 2 to about 6% of one or a mixture of water soluble alkali metal pyrophosphates and about 0.1 to about 2% of said copolymer.

11. A method as defined in claim 10 wherein said copolymer has a molecular weight of about 70,000.

* * * * *